United States Patent
Rowlandson et al.

(10) Patent No.: US 8,899,478 B2
(45) Date of Patent: Dec. 2, 2014

(54) SYSTEM AND METHOD FOR MEDICAL DATA TRANSFER

(75) Inventors: Gordon Ian Rowlandson, Milwaukee, WI (US); Tyler M. Brown, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 538 days.

(21) Appl. No.: 13/223,883

(22) Filed: Sep. 1, 2011

(65) Prior Publication Data

US 2013/0056535 A1 Mar. 7, 2013

(51) Int. Cl.
| | |
|---|---|
| *G06F 17/00* | (2006.01) |
| *G06F 7/00* | (2006.01) |
| *G07B 15/02* | (2011.01) |
| *G06K 15/00* | (2006.01) |
| *G06K 7/10* | (2006.01) |
| *G06K 7/14* | (2006.01) |
| *G06F 19/00* | (2011.01) |

(52) U.S. Cl.
CPC .................................. *G06F 19/3406* (2013.01)
USPC ........... 235/380; 235/375; 235/376; 235/384; 235/462.01; 235/454; 235/462.13

(58) Field of Classification Search
USPC ..................... 235/375, 376, 384, 462.01, 454, 235/462.13, 380
See application file for complete search history.

(56) References Cited

U.S. PATENT DOCUMENTS

| | | | |
|---|---|---|---|
| 4,835,372 A * | 5/1989 | Gombrich et al. ............ | 235/375 |
| 4,916,441 A * | 4/1990 | Gombrich ...................... | 345/169 |
| 5,630,664 A * | 5/1997 | Farrelly ......................... | 600/508 |
| 7,578,432 B2 * | 8/2009 | Libin et al. ..................... | 235/375 |
| 2002/0035637 A1 * | 3/2002 | Simmon et al. ............... | 709/234 |
| 2002/0188472 A1 * | 12/2002 | Fujisaka et al. ................. | 705/2 |
| 2003/0046109 A1 * | 3/2003 | Uchikubo ......................... | 705/2 |
| 2004/0030586 A1 * | 2/2004 | Cucchiara et al. ............... | 705/3 |
| 2005/0184153 A1 * | 8/2005 | Auchinleck .................... | 235/385 |
| 2006/0180659 A1 * | 8/2006 | Loffredo et al. .............. | 235/380 |
| 2006/0259463 A1 * | 11/2006 | Crucs ................................ | 707/3 |
| 2007/0125844 A1 * | 6/2007 | Libin et al. ..................... | 235/380 |
| 2007/0138253 A1 * | 6/2007 | Libin et al. ..................... | 235/375 |
| 2007/0233049 A1 * | 10/2007 | Wehba et al. .............. | 604/890.1 |

(Continued)

OTHER PUBLICATIONS

Centricity® Perioperative Manager, Audit Viewer, User's Manual, 2024281-003 Revision E; May 11, 2007; pp. 1-17.

(Continued)

*Primary Examiner* — Daniel Walsh
(74) *Attorney, Agent, or Firm* — Andrus Intellectual Property Law, LLP

(57) ABSTRACT

A system for transferring medical data includes a computer network upon which an electronic medical record of a patient is stored. A mobile computer presents a bar code on a graphical display. A medical device is communicatively connected to a bar code scanner and receives patient information and mobile computer information from the bar code scanner. The medical device further performs a medical test to generate test result data. The test result data is transmitted to the mobile computer based upon the received mobile computer information. A method of medical data transfer includes receiving a medical data transfer request. A bar code is scanned to input the patient information and mobile computer information into the medical device. A medical test is performed with the medical device to produce test result data that is transmitted to the mobile computer based upon the mobile computer information.

20 Claims, 3 Drawing Sheets

(56) References Cited

U.S. PATENT DOCUMENTS

| | | | |
|---|---|---|---|
| 2008/0149701 A1* | 6/2008 | Lane | 235/375 |
| 2009/0048870 A1* | 2/2009 | Godshall et al. | 705/3 |
| 2009/0121009 A1* | 5/2009 | Auchinleck | 235/375 |
| 2010/0169121 A1* | 7/2010 | Herbst et al. | 705/3 |
| 2010/0217623 A1* | 8/2010 | Schoenberg et al. | 705/3 |
| 2010/0219241 A1* | 9/2010 | Corwin et al. | 235/375 |
| 2010/0267049 A1* | 10/2010 | Rutter et al. | 435/7.1 |
| 2010/0287006 A1* | 11/2010 | Cannon et al. | 705/3 |
| 2012/0059911 A1* | 3/2012 | Randhawa et al. | 709/219 |
| 2012/0067944 A1* | 3/2012 | Ross | 235/375 |
| 2012/0215552 A1* | 8/2012 | Goldschmidt | 705/2 |

OTHER PUBLICATIONS

ECGenius. MUSE cardiology information system; General Electric Company, 2005.

MUSE™ Cardiology Information System Service Manual, 2002783-027; Revision Z; 2009; pp. 1-206.

Kuo et al, A 2D Barcode Validation System for Mobile Commerce; Advances in Grid and Pervasive Computing; May 10, 2010; Springer Berlin Heidelberg; pp. 150-161.

European Search Report dated Dec. 12, 2012.

* cited by examiner

SYSTEM AND METHOD FOR MEDICAL DATA TRANSFER

BACKGROUND

The present disclosure is related to the field of medical data transfer. More specifically, the present disclosure is related to systems and methods for directing the transfer of medical data to and from a mobile computer.

With the advent of the electronic medical record (EMR), diagnostic tests and/or images ordered through the EMR must be linked to specific patient encounters and require patient identification information so that the tests and/or images can be effectively acquired, processed, reviewed, edited, and routed for billing. All of this data transfer must be done within a system in which data security is an important consideration. Also, within a medical facility, a large number of varied brands, models, and versions of medical devices with varying communicative abilities must be integrated into the EMR system as a whole.

Therefore, systems and methods that improve medical data work flow and medical device productivity in a secure manner can improve clinician convenience and efficiency.

BRIEF DISCLOSURE

A system for transferring medical data includes a computer network upon which an electronic medical record (EMR) of a patient is stored. The EMR includes patient demographic information, patient medical data, and test result data. A mobile computer includes a graphical display and the mobile computer is communicatively connected to the computer network. Upon receiving an input from a clinician, the mobile computer presents a bar code on the graphical display that includes at least patient information and a mobile computer information encoded in the bar code. A bar code scanner reads the bar code off of the graphical display. A medical device is communicatively connected to the bar code scanner and the medical device receives the patient information and mobile computer information from the bar code scanner. The medical device further performs a medical test to generate test result data. The test result data are transmitted to the mobile computer based upon the received mobile computer information.

A method of medical data transfer includes receiving a medical data transfer request with a mobile computer. The medical data transfer request is transmitted to a computer network that includes an electronic medical record (EMR) of a patient. A bar code is generated with the computer network. The bar code encodes at least patient information and mobile computer information that identifies the mobile computer. The bar code is presented on a graphical display of the mobile computer. The presented bar code is scanned with a bar code reader of a medical device to input the patient information and the mobile information into the medical device. A medical test is performed with the medical device to produce test result data. The test result data are transmitted to the mobile computer based upon the mobile device identification number.

DETAILED DISCLOSURE

Figure 1:
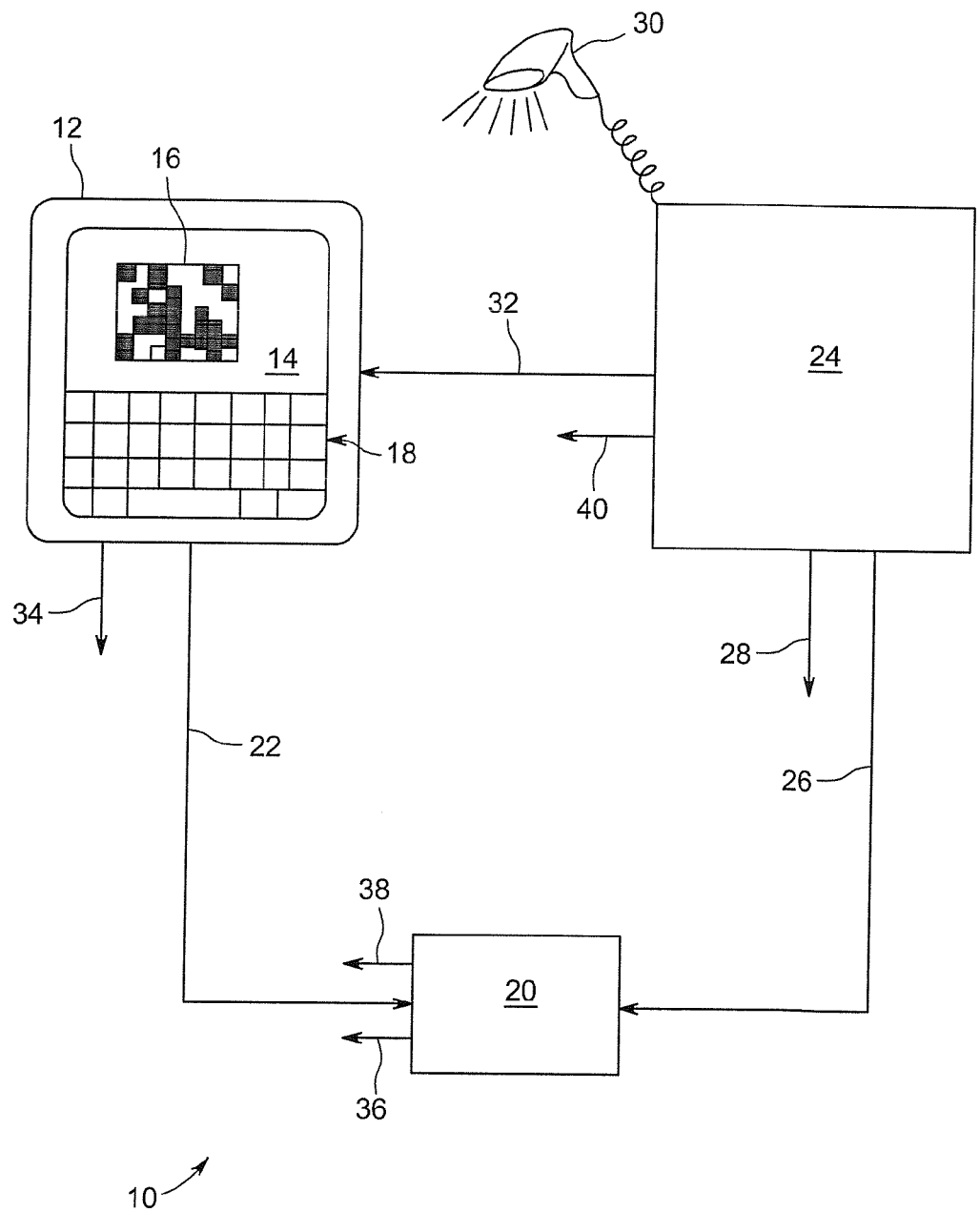
FIG. 1 is a system diagram of an embodiment of a system for transferring medical data.

FIG. 1 depicts a diagram of a system 10 for transferring medical data. The system 10 includes a mobile computer 12 which is exemplarily a smartphone, a tablet computer, or a laptop computer. In practice, a clinician that is treating a patient keeps the mobile computer 12 in the clinician's possession and carries the mobile computer 12 from room to room visiting a series of patients. In other embodiments, the clinician is visiting a patient outside of a hospital setting, such as at home or another remote location. Therefore, in embodiments, the mobile computer 12 is kept in the possession of a specific clinician who uses the mobile computer 12 within the system 10 as disclosed herein.

The mobile computer 12 includes a graphical display 14 which is operable to present a bar code 16 as will be described in further detail herein. The bar code 16 as depicted in FIG. 1 is a two dimensional bar code; however, it is understood that in alternative embodiments one dimensional or three dimensional bar codes may also be presented.

The mobile computer 12 further includes a user input device 18 which is exemplarily depicted as a virtual QWERTY keyboard presented on the graphical display 14, in which case, the graphical display 14 is a touch-screen graphical display. In alternative embodiments, it is understood that various other types of user input devices, including, but not limited to, physical keyboards may be used as the user input device 18.

The system 10 further includes a computer network 20 that operates various healthcare IT systems and programs. They include, but are not limited to, cardiology information systems, picture archiving and communication systems (PACS), electronic medical records (EMR), and/or practice management systems; however, these types of computer network systems are only intended to be exemplary and are not limiting on the scope of computer networks that may be used. Two specific non-limiting examples include the MUSE system available from GE Healthcare and the Centricity system available from GE Healthcare. It is understood that such a computer network 20 may be located and/or operated by a hospital, or may be a computer network that is located remote from a hospital or the clinicians using the system. In still further embodiments, the computer network can be operated by a third party rather than a hospital that uses the computer network.

The computer network 20 is connected to the mobile computer 12 by a data connection 22. The data connection 22 is exemplarily a wireless data connection which may be use RF or cellular communication platforms; however, it will be recognized that alternative communication platforms may be used for the data connection 22. The computer network 20 and the mobile computer 12 are able to achieve wireless bi-directional communication across the data connection 22. In some embodiments, wireless data connections are achieved by a wireless data connection wherein both the mobile computer 12 and the computer network 20 accessing an intermediate server or computer network (not depicted) that facilitates data transfer between the mobile device 12 and the computer network 20.

The system 10 further includes a medical device 24. In embodiments, the medical device 24 is an electrocardiographic (ECG), imaging, or blood pressure monitoring device. In still further embodiments, the medical device 24 may be a procedure cart that is specifically designed and adapted to facilitate a clinician performance of a procedure, exemplarily a procedure that is used to perform an invasive test on the patient, exemplarily, but not limited to, blood pressure catherization. In still further embodiments, the medical device 24 may be a therapeutic device, that can operate to perform a physiological test on the patient. One non-limiting example of such an embodiment is a mechanical ventilation system that can perform a test of patient functional residual capacity. In still further embodiments, the medical device 24 may be laboratory equipment that is used to perform analysis on samples from a patient, a non-limiting example of which may include spectroscopy of a fluid obtained from the patient.

The medical device 24 is connected to the computer network 20 by a data connection 26. The data connection 26 can be a variety of data connections, including wireless connections that exemplarily use RF or cellular communication platforms, wired data connections that use a local area network (LAN) or serial communication platform (if the medical device and computer network are connected by such a platform), or a physical data transfer that relies upon a physical computer readable medium, exemplarily an SD card or a flash drive that enables a clinician or technician to physically transfer data from the medical device 24 to the hospital computer network 20.

Test result data 28 is transferred from the medical device 24 to the computer network 20 using the data connection 26. As disclosed above, one non-limiting example of the medical device 24 is an ECG device. Such an embodiment will be exemplarily used herein in describing the system 10 and it will be understood that the description has no limiting effect on the scope or location of the medical devices that may be included within this system as disclosed above. In the embodiment wherein the medical device 24 is an ECG device, the test results may include electrocardiographic information obtained from the patient.

The medical device 24 further includes a bar code scanner 30 that is communicatively connected to the medical device 24 or is an integral part of the medical device 24. The bar code scanner 30 operates as an input device for the medical device 24, whereby the bar code scanner 30 scans a bar code to input data into the medical device 24. Typically, when a patient is admitted into a hospital or clinical setting, the patient receives a wristband with a bar code. The bar code on the wristband includes basic patient identifying information, exemplarily a patient ID number that is used to verify the patient's identity and to connect the patient to the patient's EMR. The bar code scanner 30 operates to read this basic information to identify the patient.

As will be described in further detail herein, embodiments of the medical device 24 are communicatively connected by a data connection 32 to the mobile computer 12. Such a data connection 32 is exemplarily a wireless data connection that exemplarily uses an RF or cellular communication platform.

In operation of the system 10 depicted in FIG. 1, a clinician carries a mobile computer 12 as the clinician travels to visit each patient or visit a patient that has been brought to a location with a particular medical device 24. The medical device 24 requires various patient information in order to properly set up the medical device 24 to perform a medical test on the patient and to preferably create the test result data 28 upon completion of the test.

Input of medical information into the medical device 24 can be a challenge, particularly when mobile medical devices are used, as cost and portability considerations weigh against robust user input devices integrated into the medical device. Furthermore, the manual entry of medical data into the medical device presents a time consuming task for a clinician to undertake before initiating a medical test or procedure. Additionally, the manual entry of data suffers from transcription errors.

Currently when a patient is admitted into hospital or clinical care, the patient receives a bar code, exemplarily in the form of a bar code printed on a wrist band, that identifies the patient with a patient identification which is exemplarily a patient identification number. The patient wrist band can be scanned by the bar code scanner 30 to enter the patient identification into the medical device 24. While this provides the minimum information required to link the test results to the patient for storage and processing of the test results, additional patient information more specific to the test or procedure to be performed may be beneficial to the medical device 24.

Therefore, in the system 10, the clinician operates the mobile computer 12 to input patient information and other information regarding the test or procedure to be performed using the medical device 24 into the mobile computer 12. This patient and test information 34 is sent along data connection 22, as a medical data transfer request, to the computer network 20.

The patient and test information 34 identifies the patient, such as with the patient identification number, the clinician, the test or procedure to be performed, and an identification of the mobile computer 12. The identification of the mobile computer 12 may include an Internet protocol (IP) address, cell phone number, email address, or other electronic identification that will be used by the system 10 herein to direct communications back to the mobile computer 12. The computer network 20 updates the patient EMR to reflect that the clinician has requested the test or procedure for the patient.

The computer network 20 creates a bar code file 36 that is transmitted back to the mobile computer 12 across the data connection 22. The bar code file 36 is exemplarily an image file such as a .JPEG or .PDF file format that includes an image of a bar code. As noted above, the bar code in the bar code file 36 may be a one dimensional, two dimensional, or three dimensional bar code; however, this is not intended to be limiting on the particular format of the bar code used within the system as disclosed herein. The bar code in the bar code file 36 encodes the patient and test information 34 entered by the clinician, and also can include additional information added by the computer network 20. In one example, the computer network 20 adds additional patient information from the patient's EMR that is required in the performance of the test or procedure. This may include patient demographic, patient diagnosis, other physiological or test result data recently acquired from the patient.

In alternative embodiments two or more bar codes are presented and scanned by the bar code scanner 30 of the medical device 24. In one embodiment, the bar code file 36 encodes the patient and test information 34 into a plurality of bar codes. These are either presented sequentially or simultaneously by the mobile computer for scanning. In another embodiment, the patient identification is scanned off of a wristband on the patient (as described above) while additional patient and test information 34 is encoded into one or more bar codes presented by the mobile device.

In many modern healthcare information technology systems, an order number is required for any test or procedure that is performed on a patient. The order number is used for quality control, medical record compliance, billing, and reimbursement procedures. In some clinical settings, the order number cannot be generated at a remote device, and must come from a centralized location, exemplarily the computer network 20. Therefore, the computer network 20 can generate the order number based upon the patient and test information 34 received by the computer network 20, and the data stored in the patient's EMR. The order number for the test or procedure to be performed can further be encoded into the bar code in the bar code file 36.

In an alternative embodiment, the order or requirement for a patient test comes from an operator or manager using the computer network 20. In such a case, the operator or manager can create a test request that is pushed, sent, or broadcast to one or more medical devices. The test request includes a barcode or an identification of a location on the computer network 20 wherein the bar code is accessible. The recipient of the test request accesses the barcode encoded with order number and other test information that is entered into the mobile device 24 using the bar code scanner 30.

The mobile computer 12 receives the bar code file 36 and presents the encoded data from the bar code file 36 as the bar code 16 on the graphical display 14 of the mobile computer 12. The bar code scanner 30 of the medical device 24 is used to enter all of the encoded information from the bar code 16 into the medical device 24. In this manner, more medical information is entered into the medical device 24 that facilitates the performance of the test or procedure with the medical device 24 and new pieces of information, including an order number and a mobile computer identification are provided to the medical device 24 which facilitate further features of the system 10 as will be disclosed in detail herein. This data transfer is provided in a manner that increases clinician efficiency, reduces transcription error, and provides security in the transaction of patient medical data. In an alternative embodiment, the medical device compares the patient information from the scanned wristband bar code to the patient information from the scanned bar code image presented on the graphical display 14 to verify or recheck that the scanned patient information matches or pertains to the same patient.

The medical device 24 is used by the clinician to perform the test or procedure on the patient. As disclosed above, the test or procedure performed with the medical device 24 generates test result data. In various embodiments of the system 10, the medical device 24 can take one or more actions with the test result data.

In one embodiment, the test result data 28 is transmitted from the medical device 24 to the computer network 20 with the data connection 26, as described above. The test result data 28 includes the patient identification, the order number, and the mobile computer identification as received from the scanned bar code 16 presented by the mobile computer 12. The computer network 20 receives the test result data, including the patient identification, order number, and mobile computer identification and uses the patient identification and order number to confirm and properly store the test result data in the patient's EMR and elsewhere, if necessary, within the computer network 20. The computer network 20 uses the mobile computer identification to transmit the test result data 38 on data connection 22 back to the mobile computer 12, such that the clinician that ordered the medical procedure in the first place, is notified of the test result data upon receipt of that test result data by the computer network 20. This creates and completes a feedback loop that automatedly directs the test result data to the mobile device associated with the clinician and is presumably most interested in the information provided by the test result data.

In alternative, or in additional embodiments, the medical device 24 uses the received mobile computer identification to transmit the test result data 40 directly back to the mobile computer 12, such as on data connection 32. In such an embodiment, the clinician associated with the mobile computer 12 receives automated feedback with the test result data directly from the medical device 24, as soon as the test result data is available. The medical device 24, may still, in embodiments, transmit the test result data 28 to the computer network 20 for storage and update of the patient's EMR.

In a further embodiment, the bar code file 36 further encodes multiple mobile computer identifications instead of or in addition to the identification of the mobile computer used to present the bar code. In such embodiments either the medical device 24 or the computer network 20 provides the test result data to the multiple mobile computers identified in the bar code. These multiple mobile computers may be mobile computers associated with various clinicians, managers, or technicians, and may be used for redundancy purposes, management/overview, or to account for shift changes.

In still further embodiments, the computer network 20 or the medical device 24, rather than transmitting the actual test data to each of the identified mobile computers, pushes the test data to an accessible location, such as a website that is operated by either the computer network 20 or a third party, while a link, log in, or other access key is sent to the mobile computers for streamlined access to the test data, exemplarily through the Internet.

Figure 2:
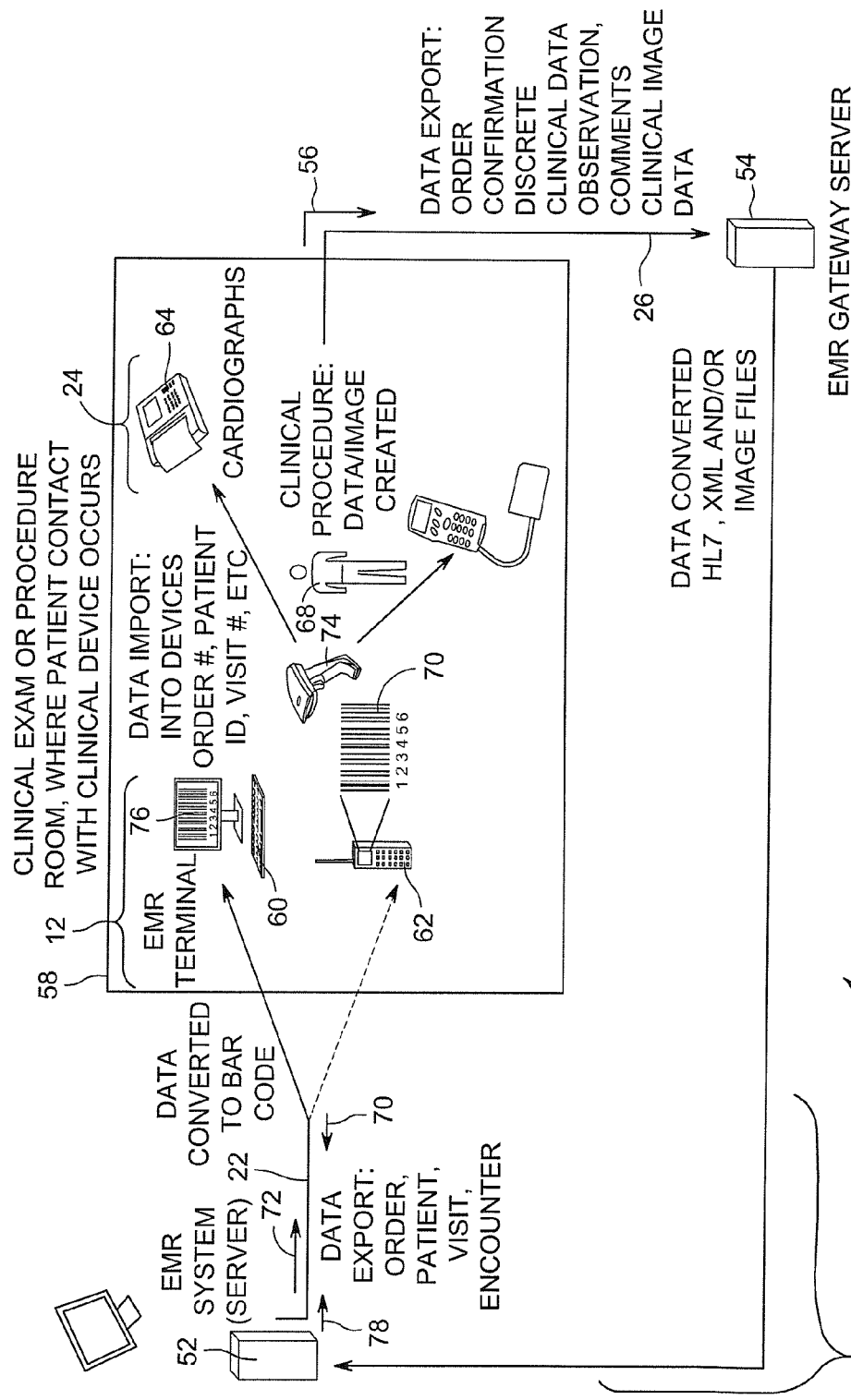
FIG. 2 is a system diagram of an alternative embodiment of a system for transferring medical data.

FIG. 2 depicts an alternative embodiment of a system 50 for transferring medical data. The system 50 is one of many alternative configurations of the system 50 using the components as disclosed herein. Generalized references to the system 10 depicted in FIG. 1 are used to point out correspondences between the embodiments.

The system 50 includes the same generalized components as shown in the system 10 of FIG. 1, including a mobile computer 12, a medical device 24, and a computer network 20 exemplarily, the computer network 20 is a hospital computer network 20 or operated by a hospital or other medical facility; however, such a system may service the IT needs of an entire hospital system and should not be considered to be limited to a computer network within a single building. However, additional features of the system 50 will be disclosed herein.

The system 50 depicts the hospital computer network 20 as including both an EMR system server 52 and an EMR gateway server 54. This distinction further highlights features of the system 50 as disclosed herein. Due to requirements and regulations for the security of patient medical data, the EMR gateway server 54 is designed to receive and accept test results or other patient medical information, exemplarily test result data 56 from a wide variety of medical devices, computers and data formats, than the EMR gateway 54 is designed to transmit medical data out to these devices. One such way in which data transactions are limited is that the patient data must be converted from the manner in which it is received from the various medical devices or computers as compared to the formats (exemplarily HL7) in which the data is stored in the EMR system 52. While this data conversion is relatively straightforward for the EMR gateway 54 to convert to the EMR system file formats, the same is not the case to convert the standardized EMR system file format into the formats used by each different and model of medical device or computer within a hospital system. Therefore, despite the existence of data connection 26, as described above through which test result data 56 is transmitted, the medical device 24 is unable to access the patient information stored in the EMR system 52 directly.

As noted above, the mobile computer 12 and the hospital computer network 20 are communicatively connected by a data connection 22. More specifically, the EMR system 52 is connected to the mobile computer 12 by a data connection 22. As depicted in system 50 of FIG. 2, the mobile computer 12 and the medical device 24, at the time of an initiation of a medical test or procedure, reside within the same clinical room 58. In such an example, the clinician, whom is associated with the mobile computer 12, which exemplarily may be an EMR terminal 60 that operates on a computer found on a cart, or a laptop computer carried by the clinician, or the mobile computer may further be a mobile device 62 such as, but not limited to, a tablet computer, or another hand-held web enabled device associated with the clinician and the medical device 24 which may exemplarily include, but is not limited to cardiographs 64 or a Holter ECG monitor 66 that is associated with the patient 68. Therefore, while the clinician is in proximity with the patient 66, the clinician can provide the patient identification information, request the medical test or procedure, and provide the mobile computer identification of the mobile computer associated with the clinician across the data connection 22 to the EMR system 52.

As noted above, the EMR system 52 takes the received medical data and any additional data that may be required from the patient's EMR and, in some embodiments, generates an order number for the medical test or procedure and converts this into a bar code file 72 that is transmitted back to the mobile computer 12. The creation of the bar code file 72 transmits the sensitive medical data of the patient in a secure manner, such that the clinician is able to control the use of the patient medical data by the physical act of scanning the bar code with a bar code scanner 74 associated with the medical device 24. Furthermore, the conversion of the medical data to the bar code file 72 places the medical data in a standardized format for transmission and entry into any of a variety of medical devices 24, rather than the conversion of the medical data by the EMR system 52 to a suitable and secure data format that is usable by the disparate manufacturers and models of the different medical devices 24.

After the medical data has been entered into the medical device 24 using the bar code scanner 74 to scan a bar code 76 that is presented on a graphical display of one of the mobile computers 12, the medical device 24 is operated to perform the ordered test or procedure. The test result data 56 produced by the medical device 24 includes not only the data generated from the performance of the test or medical procedure, but also includes the patient's identification, order number, and mobile computer identification provided to the medical device by scanning the bar code 76. The EMR gateway server 54 receives this information and uses the additional data such as the order number to confirm and properly format, process, and store the test result data on the patient's EMR stored on the EMR system 52. The mobile computer identification is also provided to the EMR system 52 and the EMR system 52 uses that mobile computer identification to automatedly transmit the test result data 78 back to the mobile computer 12 used by the clinician to initiate the test or medical procedure. However, it is to be understood that by this time it is likely that the clinician may have moved to another location and will not be in the clinical room 58 with the patient 68, but rather in a different location within the medical facility. However, it is to be that in some embodiments, the clinician may still be in the clinical room 58 with the patient 68 at the time that the test result data 78 is automatically transmitted to the mobile computer 12 associated with the clinician. In these instances, the clinician is able to provide direct and timely feedback to the patient 68 at the earliest time that the test results are available.

Figure 3:
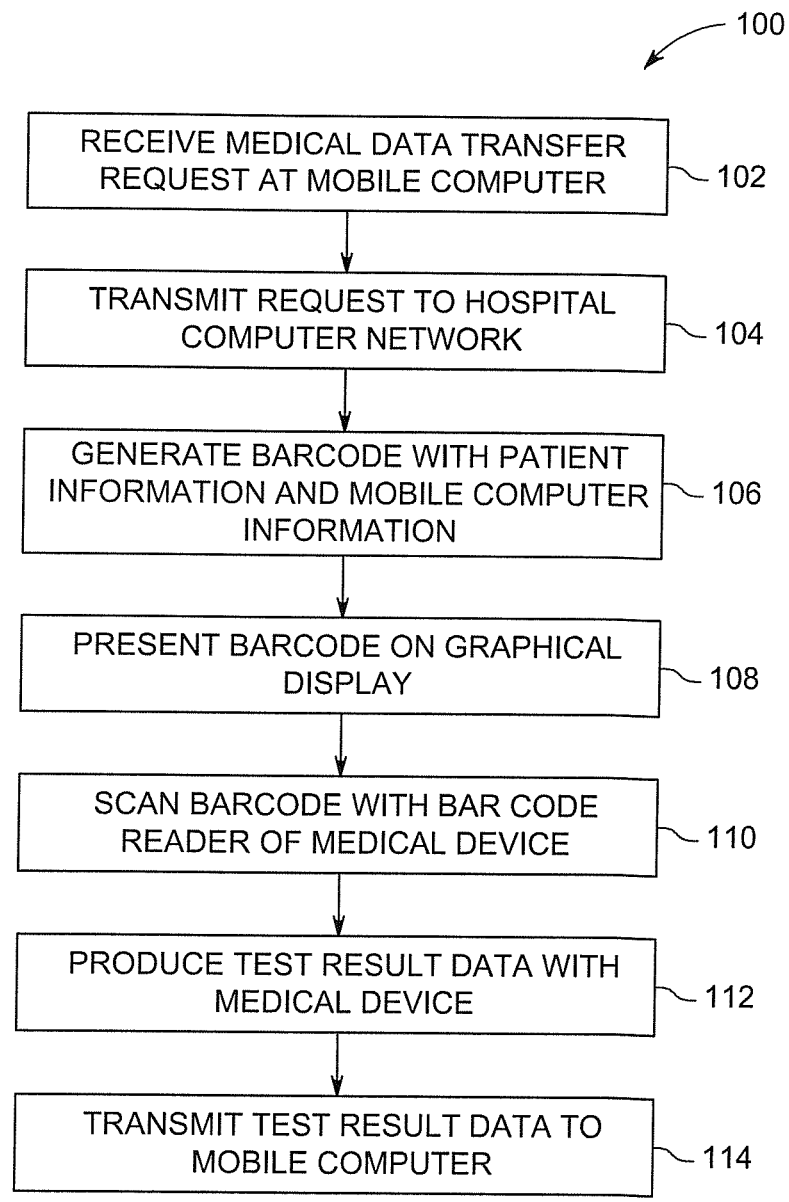
FIG. 3 is a flow chart that depicts an embodiment of a method of medical data transfer.

FIG. 3 is a flow chart that depicts an embodiment of a method 100 of medical data transfer. At 102 a medical data transfer request is received at a mobile computer. As described above, the mobile computer can be an EMR terminal or a mobile device, including, but not limited to a smartphone or a tablet computer. The medical data transfer request at 102 is typically input by a clinician that is in proximity with a patient and the clinician desires that a particular medical test or procedure be performed on the patient using a medical device.

The received medical data transfer request is transmitted to a hospital computer network at 104. As described above, the hospital computer network may be any of a variety of hospital information technology systems, including those systems that include a patient electronic medical record (EMR). In response to the medical data transfer request received at 104, the hospital computer network, at 106, generates a bar code with patient information and mobile computer information at 106. The patient information is information regarding the patient, some of which may have been accessed from the patient's EMR which otherwise identifies the patient, and/or provides demographic, diagnosis, or physiological data regarding the patient that is needed by the medical device to perform the test or medical procedure. Additionally, the patient information can include an order number that is generated for the test or medical procedure that requires the request of medical data transfer. The mobile computer information encoded in the bar code generated at 106 identifies the mobile computer with which the medical data transfer request was received, such that further communications as are described herein can be provided directly to the mobile computer associated with the clinician that placed the medical data transfer request. The mobile computer information can exemplarily be an IP address, email, phone number, or other identifying information.

It is to be understood that in an alternative embodiment, the bar code with the patient information and mobile computer information generated at 106 could alternatively be generated by the mobile computer, in embodiments of the system that are configured for such operation. Such embodiments would require additional data storage and computational requirements for the mobile computer to enable direct access to the patient data and for bar code generation requirements.

The bar code generated at 108 is presented on a graphical display of the mobile computer at 108. The bar code that is presented on the graphical display at 108 is exemplarily two dimensional, however, this is not intended to be limiting on the scope of dimensions required in the bar codes presented on the graphical displays. In this manner, the bar code presented on the graphical display at 108 is specifically generated for the secure transmission and data entry of only the medical data to be transferred to the medical device to conduct the test or medical procedure.

The bar code presented in 108 is scanned with a bar code reader of a medical device at 110. The scanning of the presented bar code with the bar code reader imports the patient information data into the medical device for use in the medical test or procedure and further imports the information or instructions for data export with the mobile computer information in the bar code. The bar code reader of the medical device may scan the information from the generated bar code into a plurality of defined and/or undefined data fields in the medical device, and within these fields, the data from the scanned bar code is stored for use by the medical device. The medical device uses the patient information obtained by scanning the bar code to produce test result data at 112. The test result data can be any of a variety of test result data format, including images, wave forms, numerical values, comments, observations, or other types of medical test or procedure results.

Finally, at 114 the test result data produced by the medical device is transmitted to the mobile computer using the mobile computer information entered into the medical device by scanning the bar code. In one embodiment, the medical device itself transmits the test result data back to the mobile computer according to the mobile computer information. In an alternative embodiment, the medical device transmits the test result data to the hospital computer network along with the mobile computer information and the hospital computer network transmits the test result data to the mobile computer.

In embodiments, wherein the test result data from the medical device is transmitted to the hospital computer network along with the mobile computer information, the hospital computer network may store the test result data in the patient's EMR that is stored at the hospital computer network.

It is to be recognized that in alternative embodiments, additional data or information can be encoded into the bar code presented on the graphical display and scanned into the medical device. Such additional data or information may include an order number, such as must be generated by the hospital computer network in order to confirm authorization of the medical test or procedure. This order number is further used to billing and compliance purposes. The inclusion of the order number encoded into the bar code further enters the order number into the medical device and therefore the medical device can transmit the test result data in conjunction with the order number for additional analysis or information to ensure that the test result data is properly authorized, billed, and stored in the EMR of the correct patient.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for transferring medical data, the system comprising:
    a hospital computer network upon which an electronic medical record (EMR) of a patient is stored, the EMR comprising patient demographic information, patient medical data, and patient test result data;
    a mobile computer that includes a graphical display and the mobile computer is communicatively connected to the hospital computer network, upon receiving an input from a clinician, the mobile computer presents a bar code on the graphical display that comprises at least patient information and mobile computer information encoded in the bar code;
    a bar code scanner configured to read the bar code off of the graphical display; and
    a medical device being communicatively connected to the bar code scanner and receives the patient information and mobile computer information from the bar code scanner, the medical device further performs a medical test to generate test result data, the test result data being transmitted to the mobile computer based upon the received mobile computer information.

2. The system of claim 1, wherein the mobile computer generates the bar code.

3. The system of claim 1, wherein the mobile computer provides the input from the clinician to the hospital computer network, and the hospital computer network generates the bar code and transmits the generated bar code to the mobile computer.

4. The system of claim 3, wherein the mobile computer provides an identification to the hospital computer network, such that the mobile computer information encoded in the bar code generated by the hospital computer network identifies the mobile computer.

5. The system of claim 3, wherein the bar code generated by the hospital computer network is transmitted to the mobile computer as an image file.

6. The system of claim 1, wherein the medical device transmits the medical test results, patient information, and mobile computer information to the hospital computer network, and the medical test results are stored in the EMR of the patient.

7. The system of claim 6, wherein the hospital computer network transmits the medical test results to the mobile computer identified by the mobile computer information.

8. The system of claim 6, wherein the medical device integrates the patient information and mobile computer information into the medical test results for transmission to the hospital computer network.

9. The system of claim 1, wherein the bar code further comprises a medical test order number, wherein the medical test order number is received by the medical device and transmitted to the hospital computer network.

10. The system of claim 1, wherein the bar code scanner scans patient information off of a barcode on a wristband associated with the patient into the medical device and the medical device compares the patient information off of the wristband to the patient information scanned from the bar code presented on the graphical display, to verify correspondence between the patient information scanned from the barcodes respectively on the wristband and the graphical display.

11. A method of medical data transfer, the method comprising:
    receiving a medical data transfer request with a mobile computer;
    transmitting the medical data transfer request to a hospital computer network that includes an electronic medical record (EMR) of a patient;
    generating a bar code with the hospital computer network, the bar code encoding at least patient information and mobile computer information that identifies the mobile computer;
    presenting the bar code on a graphical display;
    scanning the presented bar code with a bar code reader of a medical device and inputting the patient information and the mobile computer information into the medical device by said scanning;
    performing a medical test with the medical device and producing corresponding test result data; and
    transmitting the test result data to the mobile computer based upon the mobile computer information.

12. The method of claim 11, further comprising associating the medical test results with the received mobile computer information.

13. The method of claim 12, wherein the mobile computer information is a mobile device identification number.

14. The method of claim 11, further comprising:
    transmitting the test result data, patient information, and the mobile computer information to the hospital computer network;
    storing the test result data in the EMR of the hospital computer network;

transmitting the test result data from the hospital computer network to the mobile computer identified by the mobile computer information.

15. The method of claim 14, wherein the bar code further encodes an order number, the order number being received by the medical device and transmitted to the hospital computer network with the test result data.

16. A system for medical data transfer, the system comprising:
- an electronic medical record (EMR) server upon which an electronic medical record (EMR) of a patient is stored, the EMR server receives a medical test request from a mobile device and generates a bar code that encodes at least patient or test information from the EMR of the patient and mobile device information that identifies the mobile device and transmits the bar code to the mobile device; and
- an EMR gateway server that receives test result data from a medical device, the test result data includes the mobile device information;

wherein the EMR server automatically transmits the test result data to the mobile device based upon the received mobile device information.

17. The system of claim 16, wherein the mobile device information is a mobile device Internet protocol (IP) address.

18. The system of claim 16, wherein the medical device transmits the test result data and the mobile device information to the EMR gateway server, the EMR gateway server transmits the test result data and the mobile device information to the EMR server, and the EMR server transmits the test result data to the mobile device based upon the mobile device information.

19. The system of claim 17, wherein the EMR server further updates the EMR of the patient with the test result data.

20. The system of claim 19, wherein the EMR server further generates an order number in response to the received medical test request, encodes the order number into the bar code, and receives the order number back from the medical device along with the test result data.

* * * * *